(12) United States Patent
Satake

(10) Patent No.: US 8,231,617 B2
(45) Date of Patent: Jul. 31, 2012

(54) RADIO-FREQUENCY THERMAL BALLOON CATHETER

(76) Inventor: Shutaro Satake, Kamakura (JP)

( * ) Notice: Subject to any disclaimer, the term of this patent is extended or adjusted under 35 U.S.C. 154(b) by 1624 days.

(21) Appl. No.: 10/571,599

(22) PCT Filed: Aug. 20, 2004

(86) PCT No.: PCT/JP2004/012009
§ 371 (c)(1),
(2), (4) Date: Mar. 10, 2006

(87) PCT Pub. No.: WO2005/060848
PCT Pub. Date: Jul. 7, 2005

(65) Prior Publication Data
US 2007/0060990 A1    Mar. 15, 2007

(30) Foreign Application Priority Data
Dec. 22, 2003 (JP) ................. 2003-425214

(51) Int. Cl.
*A61B 18/12* (2006.01)
(52) U.S. Cl. .............. 606/41; 606/1; 606/40; 606/42; 606/50; 607/100; 607/110
(58) Field of Classification Search .......... 606/1–50; 607/100–110
See application file for complete search history.

(56) References Cited

U.S. PATENT DOCUMENTS

| | | | |
|---|---|---|---|
| 4,955,377 A * | 9/1990 | Lennox et al. | 607/105 |
| 5,368,591 A * | 11/1994 | Lennox et al. | 606/27 |
| 5,571,153 A | 11/1996 | Wallstén | |
| 5,603,720 A * | 2/1997 | Kieturakis | 606/191 |
| 5,624,392 A * | 4/1997 | Saab | 604/43 |
| 5,827,269 A * | 10/1998 | Saadat | 606/28 |
| 5,954,714 A * | 9/1999 | Saadat et al. | 606/28 |
| 5,957,962 A | 9/1999 | Wallstén et al. | |
| 6,019,783 A * | 2/2000 | Philips et al. | 607/105 |

(Continued)

FOREIGN PATENT DOCUMENTS

JP    8-98857    4/1996

(Continued)

OTHER PUBLICATIONS

Supplementary European Search Report issued Aug. 6, 2008 in European Application No. 04 77 1970.

(Continued)

*Primary Examiner* — Aaron Roane
(74) *Attorney, Agent, or Firm* — Wenderoth, Lind & Ponack, L.L.P.

(57) ABSTRACT

A radio-frequency thermal balloon catheter includes a catheter tube including an outer tube and an inner tube, a balloon connected to an end part of the outer tube and an end part of the inner tube, and capable of coming into contact with a target diseased part when inflated, a radio-frequency electrode placed in the wall of the balloon or inside the balloon to transmit radio-frequency current, a lead wire electrically connected to the radio-frequency electrode, a temperature sensor capable of measuring temperature inside the balloon, and a swirling current producing means for making a fluid contained in the balloon swirl in a vertical plane in the balloon so as to reduce an upper-lower temperature difference between an upper part and a lower part of the interior of the balloon due to convection of the fluid to naught.

11 Claims, 13 Drawing Sheets

U.S. PATENT DOCUMENTS

| | | |
|---|---|---|
| 6,409,747 B1 | 6/2002 | Gobin et al. |
| 6,416,533 B1 | 7/2002 | Gobin et al. |
| 6,491,710 B2 * | 12/2002 | Satake ............ 606/191 |
| 6,527,798 B2 * | 3/2003 | Ginsburg et al. ............ 607/106 |
| 6,530,946 B1 | 3/2003 | Noda et al. |
| 2002/0007138 A1 * | 1/2002 | Wilk et al. ............ 604/9 |
| 2002/0029062 A1 | 3/2002 | Satake |
| 2002/0082682 A1 * | 6/2002 | Barclay et al. ............ 623/1.22 |
| 2002/0111584 A1 | 8/2002 | Walker et al. |
| 2003/0060761 A1 | 3/2003 | Evans et al. |
| 2003/0065371 A1 | 4/2003 | Satake |

FOREIGN PATENT DOCUMENTS

| | | |
|---|---|---|
| JP | 2001-503666 | 3/2001 |
| JP | 2003-102850 | 4/2003 |
| JP | 2003-305076 | 10/2003 |
| WO | 98/22032 | 5/1998 |

OTHER PUBLICATIONS

Japanese Office Action mailed Jun. 19, 2009 for Japanese Application No. 2003-425214.

* cited by examiner

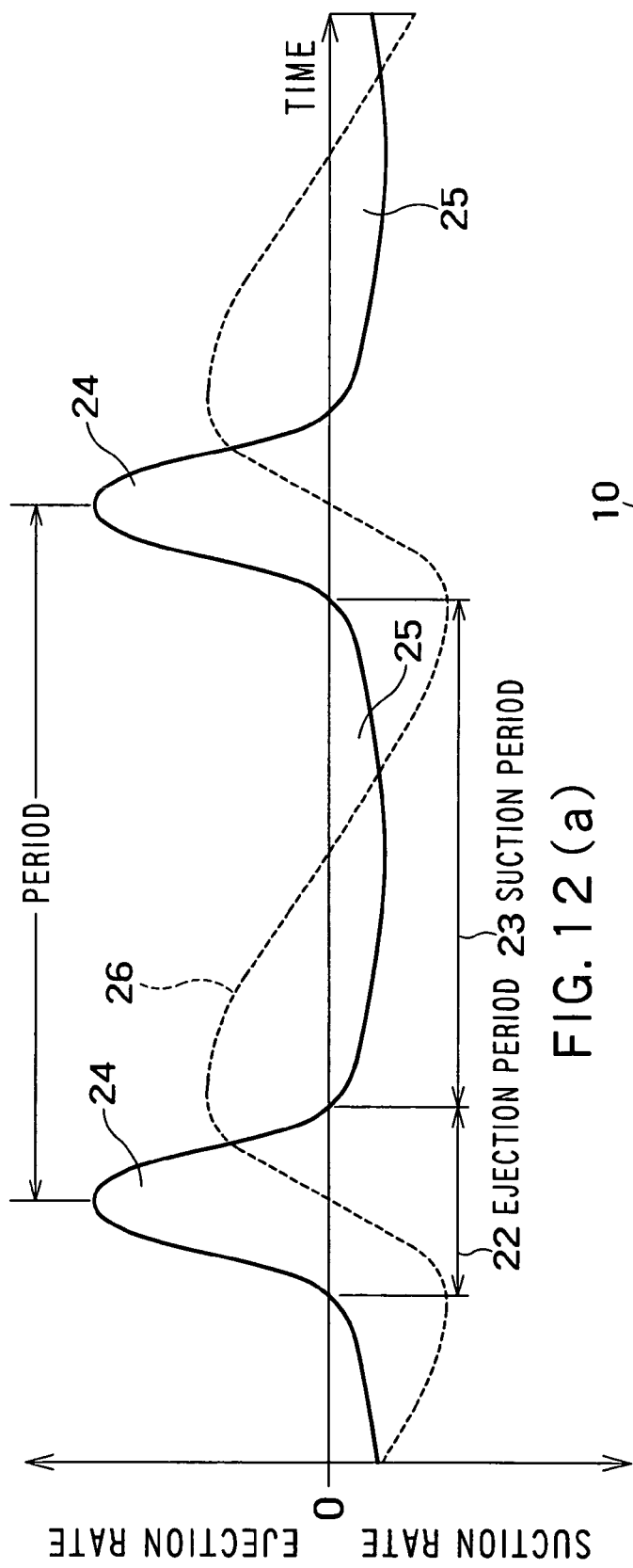
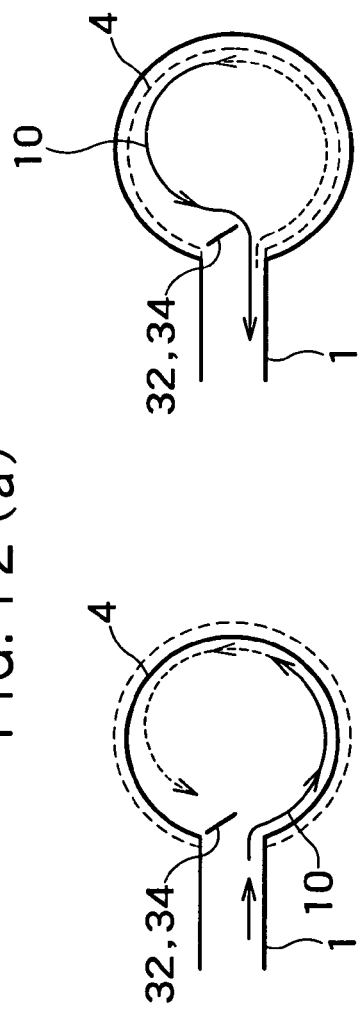
FIG. 12(a)
FIG. 12(b)
FIG. 12(c)

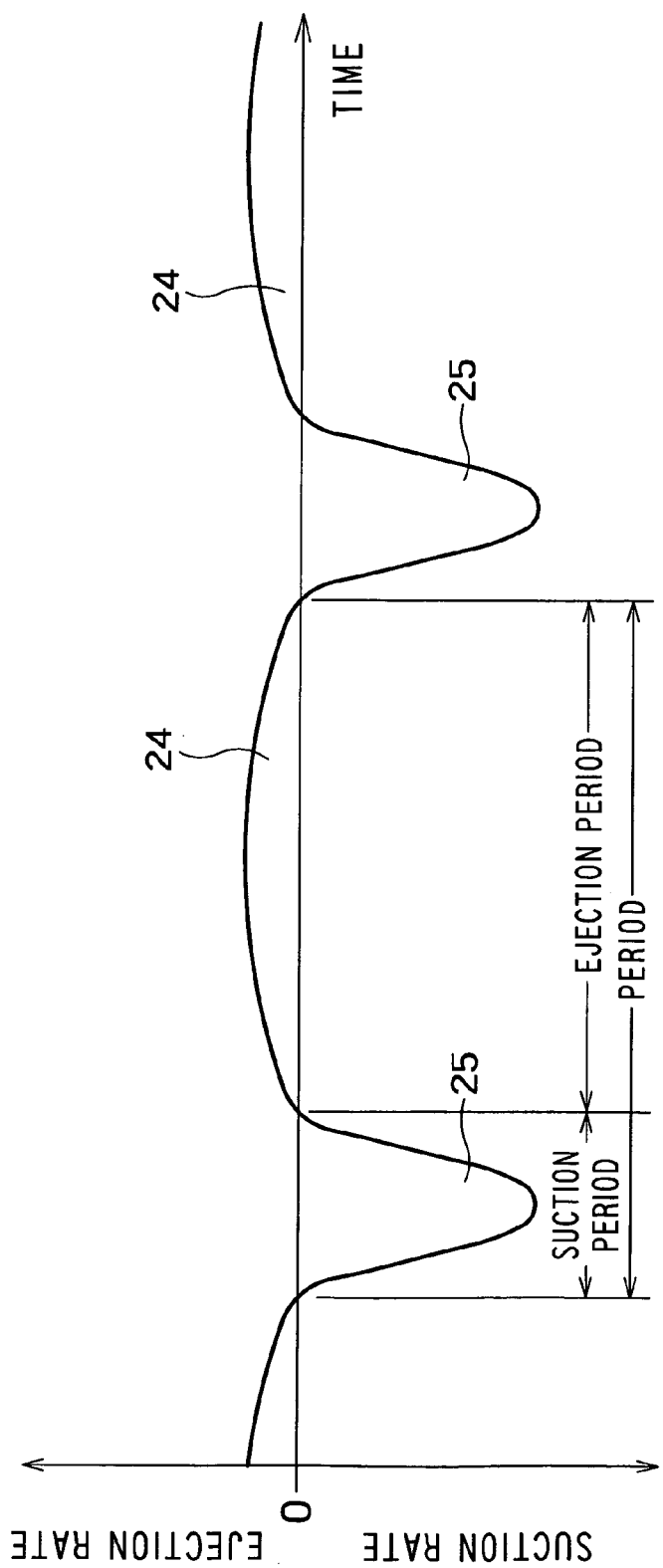
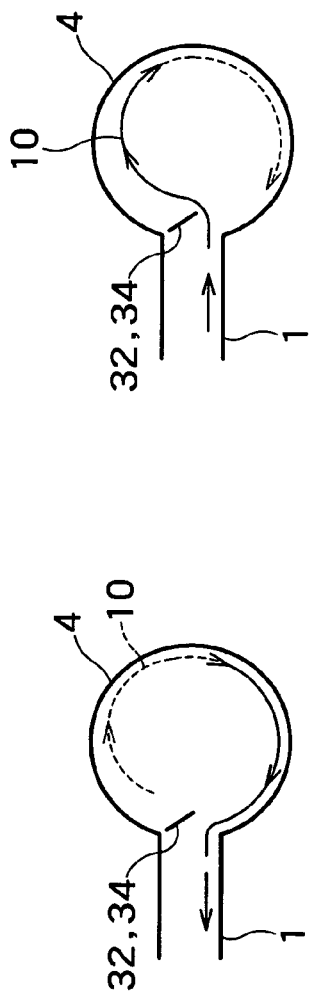
FIG. 13(a)
FIG. 13(b)
FIG. 13(c)

RADIO-FREQUENCY THERMAL BALLOON CATHETER

TECHNICAL FIELD

The present invention relates to a radio-frequency thermal balloon catheter and, more specifically, to a balloon catheter for the radio-frequency thermal treatment for cardiovascular diseases.

BACKGROUND ART

Medial treatments for diseases, such as origin of arrhythmia and arteriosclerosis, have been proposed in, for example, Jpn. Pat. Nos. 2538375, 2510428 and 2574119, U.S. Pat. No. 6,491,710 B2 and JP 2003-120850 A (JP '850). Those known medical treatments use an inflatable balloon internally provided with a radio-frequency electrode. A radio-frequency electric field is created around the radio-frequency electrode to heat tissues in contact with the balloon for treatment.

Tissues in contact with a balloon need to be heated as uniformly as possible to treat the tissues satisfactorily. A radio-frequency electrode having a three-dimensional shape cannot be disposed in perfect alignment with the balloon inside the balloon and hence the liquid contained in the balloon is heated irregularly. In addition, the liquid inside the balloon is heated unavoidably in a non-uniform temperature distribution due to convention. Hence tissues in contact with the balloon cannot be uniformly heated.

SUMMARY OF THE INVENTION

A previously proposed method of stirring a liquid contained in the balloon to solve the foregoing problems is disclosed in JP '850. When the liquid in JP '850 is simply stirred, however, both horizontal and vertical swirling currents are produced in the balloon. In the present invention, studies found that the temperature of the liquid in an upper part of the balloon is higher than that of the liquid in a lower part of the balloon owing to a vertical temperature distribution in the liquid along the direction of the gravitational force due to convection and the temperature difference between the upper and the low part of the balloon cannot be satisfactorily reduced.

In the present invention, a downward direction is parallel to the direction of the gravitational force, and an upward direction is opposite the direction of the gravitational force. The term "upper-lower temperature difference" is used herein to signify the difference between the respective temperatures of an upper and a lower part of the balloon.

Accordingly, it is an object of the present invention to solve the foregoing problems in the prior art and to provide a radio-frequency thermal balloon catheter provided with a balloon, and capable of reducing the upper-lower temperature difference due to convection to naught and of uniformly heating tissues in contact with the balloon at an optimum temperature for the safe thermal treatment of a lesion.

A radio-frequency thermal balloon catheter according to the present invention includes: a catheter tube including an outer tube and an inner tube; a balloon connected to an end part of the outer tube and an end part of the inner tube, and capable of coming into contact with a target lesion when inflated; a radio-frequency electrode placed in the wall of the balloon or inside the balloon to transmit radio-frequency current; a lead wire electrically connected to the radio-frequency electrode; a temperature sensor capable of measuring temperature inside the balloon; and a swirling current producing means or unit for making a fluid contained in the balloon swirl in a vertical plane in the balloon so as to reduce a upper-lower temperature difference between an upper part and a lower part of the interior of the balloon due to convection of the fluid to naught.

In the radio-frequency thermal balloon catheter according to the present invention, the swirling current producing means includes a vibratory driving means or unit for propagating a vibration through the fluid filling up a vibration propagating passage defined by the inside surface of the outer tube and the outside surface of the inner tube to the fluid filling up the balloon, and a vibration propagating direction deflecting means (baffle) or unit disposed near the inlet of the balloon at an end of the vibration propagating passage to deflect the direction of propagation of the vibration upward or downward in the balloon.

In the radio-frequency thermal balloon catheter according to the present invention, a period of the vibration generated by the vibratory driving means includes a fluid ejection period in which the fluid is ejected into the balloon and a fluid suction period in which the fluid in the balloon is suctioned, and the fluid ejection period is shorter than the fluid suction period and a fluid ejection rate at which the fluid is ejected in the fluid ejection period is higher than a fluid suction rate at which the fluid is suctioned in the fluid suction period, or the fluid ejection period is longer than the fluid suction period and a fluid ejection rate at which the fluid is ejected in the fluid ejection period is lower than a fluid suction rate at which the fluid is suctioned in the fluid suction period.

In the radio-frequency thermal balloon catheter according to the present invention, the product of the fluid ejection period and the fluid ejection rate is equal to the product of the fluid suction period and the fluid suction rate.

In the radio-frequency thermal balloon catheter according to the present invention, the vibration propagating direction deflecting means includes a pair of blades disposed on the opposite sides of the inner tube near the inlet part, each of the pair of blades is inclined so as to deflect the direction of propagation of the vibration propagated through the vibration propagating passage into the balloon upward or downward in the balloon.

In the radio-frequency thermal balloon catheter according to the present invention, the vibration propagating direction deflecting means includes a tube having an open end and a bottomed end and provided with first and second holes in its wall, the inner tube extends through the wall of the tube disposed with the first and the second hole vertically arranged, and the tube is inclined so as to deflect the direction of propagation of the vibration propagated through the vibration propagating passage into the balloon upward or downward in the balloon.

In the radio-frequency thermal balloon catheter according to the present invention, the vibration propagating direction deflecting means includes a pair of unidirectional valves disposed on the upper and the lower side of the inner tube near the inlet, one of the unidirectional valve opens to permit ejection the fluid into the balloon and the other unidirectional valve opens to permit suction the fluid out of the balloon.

In the radio-frequency thermal balloon catheter according to the present invention, the vibration propagating direction deflecting means includes an extension tube extending from the outer tube and having a closed end, and either an upper or a lower side part of the extension tube is provided with an opening.

In the radio-frequency thermal balloon catheter according to the present invention, the vibration propagating direction deflecting means includes an extension tube extending from the outer tube and having a closed end, and a branch tube extending from either an upper or a lower side part of the extension tube.

In the radio-frequency thermal balloon catheter according to the present invention, the catheter tube is marked with a mark indicating a position of the balloon with respect to a vertical direction.

In the radio-frequency thermal balloon catheter according to the present invention, the mark is radiopaque.

In the radio-frequency thermal balloon catheter according to the present invention, the radio-frequency electrode is wound spirally around the inner tube.

In the radio-frequency thermal balloon catheter according to the present invention, the balloon is made of a anti-thrombotic, heat-resistant, and elastic resin.

According to the present invention, the radio-frequency thermal balloon catheter is provided with the swirling current producing means for making a fluid contained in the balloon swirl up and down in the balloon so as to reduce the upper-lower temperature difference due to convection of the fluid to naught. Therefore, the radio-frequency thermal balloon catheter is capable of surely reducing the upper-lower temperature difference due to convection of the fluid to naught and of uniformly heating tissues in contact with the balloon d at an optimum temperature for the safe thermal treatment of a lesion.

When a part of the balloon in contact with tissues is kept at a temperature between 60° C. and 65° C. for a time between 3 and 5 min, a three-dimensional, transmural, necrotic layer can be safely formed without forming thrombi and without causing ulceration due to the vaporization of tissues. Thus origin of arrhythmia can be treated by cauterization. When the isolation of the pulmonary vein ostium and the cauterization of the atrial muscles around the pulmonary vein ostium are performed, the atrial fibrillations that may be otherwise caused by those treated lesion can be permanently healed. Since a circular part of the exit of the right ventricle can be transmuraly cauterized, ventricular tachycardia and ventricular fibrillation that may be otherwise caused by the treated lesion can be permanently healed.

When tissues affected by arteriosclerosis are heated at temperatures in the range of 43° C. to 45° C. for 20 min or longer, the Apotosis of inflammatory cells, such as labilizing macrophages, occurs and thereby tissues affected by arteriosclerosis can be stabilized.

The radio-frequency thermal balloon catheter can be applied to the local thermal treatment for cancer. It is known that cancer cells can be controlled and extinguished by heating the same at temperatures in the range of 43° C. to 45° C. for 20 min or longer. The radio-frequency thermal balloon catheter of the present invention can be effectively applied to the treatment for bronchogenic cancer, bile duct cancer, liver cancer and prostate cancer.

BRIEF DESCRIPTION OF THE DRAWINGS

FIGS. 12(a), 12(b) and 12(c) are views respectively showing the waveform of a vibration generated by a vibratory generator, an mode of change of the volume of the balloon and the flow of the fluid in the balloon during a ejection period, and a mode of change of the volume of the balloon during a suction period; and FIGS. 13(a), 13(b) and 13(c) are views respectively showing the waveform of a vibration generated by a vibratory generator, a mode of change of the flow of the fluid in the balloon during an ejection period, and a mode of change of the flow of the fluid in the balloon during a suction period.

-DETAILED DESCRIPTION OF THE INVENTION

Figure 1:
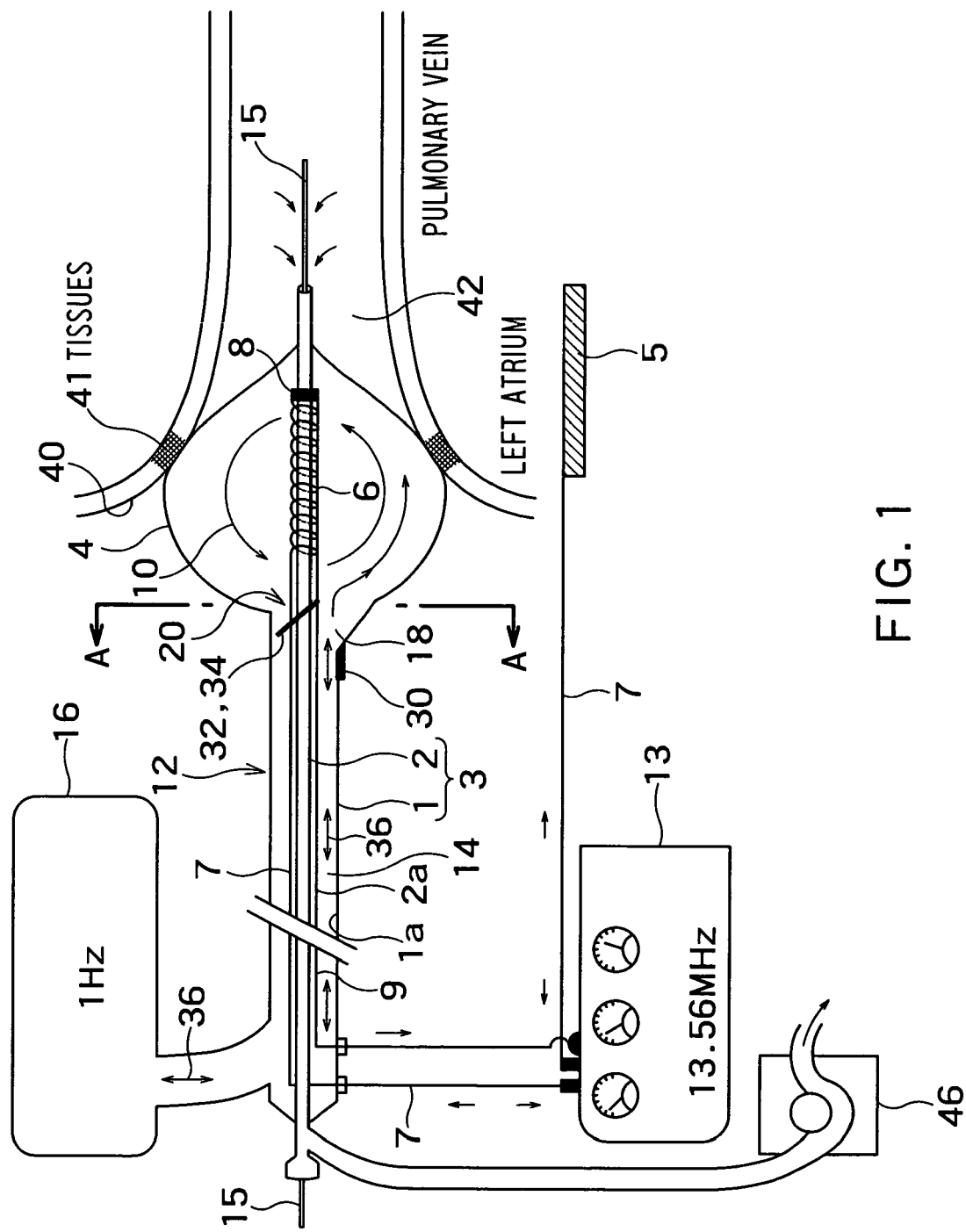
FIG. 1 is a schematic view of a radio-frequency thermal balloon catheter in a first embodiment according to the present invention in use for cauterizing a part around the ostium of the pulmonary vein near the atrium.

Radio-frequency thermal balloon catheters in preferred embodiments according to the present invention will be described with reference to the accompanying drawings.

A radio-frequency thermal balloon catheter (hereinafter, referred to simply as "balloon catheter") for the electrical isolation of the pulmonary vein ostium for a treatment for atrial fibrillation is described herein.

The balloon catheter includes a catheter tube 3 consisting of an outer tube 1 and an inner tube 2, a balloon 4 connected to an end part of the outer tube 1 and an end part of the inner tube 2, and capable of coming into contact with a target lesion when inflated, a radio-frequency electrode 6 serving as a counter to a counter electrode 5 attached to the surface of a subject's body and placed in the wall of the balloon 4 or inside the balloon 4 to supply radio-frequency power between the surface electrode 5 and the radio-frequency electrode 4, a lead wire 7 electrically connected to the radio-frequency electrode 6, a temperature sensor 8 capable of measuring temperature inside the balloon 4, a lead wire 9 connected to the temperature sensor 8, and a swirling current producing device for making a fluid contained in the balloon 4 swirl up and down in the balloon 4 so as to reduce the upper-lower temperature difference due to convection of the fluid to naught.

The fluid is a liquid, such as physiological saline, or a gas, such as carbon dioxide gas. In this description, a downward direction is parallel to the direction of the gravitational force, and an upward direction is opposite the direction of the gravitational force, and the term "upper-lower temperature difference" is used herein to signify the difference between the respective temperatures of an upper and a lower part of the balloon in a normal position for use. The outer tube 1 of the catheter tube 3 is marked with a radiopaque mark 30 (hereinafter, referred to as "impermeable mark") and indicating a position of the balloon with respect to a vertical direction.

There is a temperature difference between an upper and a lower part of the balloon 4 due to convection. The outer tube 1 is marked with the radiopaque mark 30 indicating a position of the balloon 4 with respect to a vertical direction. The radiopaque mark 30 is impermeable to x-rays. The position and attitude of a vibration propagating direction deflecting device 20 included in a swirling current producing device 12 can be known through the detection of the radiopaque mark 30 by an x-ray device.

The radio-frequency electrode 6 is wound spirally around the inner tube 2. The radio-frequency electrode 6 may be wound around an extension tube extending from the outer tube 1. The counter electrode 5 and the radio-frequency electrode 6 are connected to a radio-frequency generator 13 by lead wires 7. The radio-frequency generator 13 supplies radio-frequency power through the lead wires 7 to the counter electrode 5 and the radio-frequency electrode 6. The output of the radio-frequency generator 13 is controlled on the basis of a temperature inside the balloon 4 measured by the temperature sensor 8 so that the fluid contained in the balloon 4 is heated at a proper temperature.

The balloon 4 is made of a anti-thrombotic, heat-resistant, elastic resin. When the radio-frequency thermal balloon catheter is pressed against the ostium having a diameter in the range of 15 to 30 mm of the pulmonary vein to cauterize the atrial muscles around the ostium of the pulmonary vein, the diameter of the inflated balloon 4 is in the range of 20 to 40 mm.

The balloon 4 is connected to an end part of the outer tube 1 and an end part of the inner tube 2. The inner tube 2 is slidable relative to the outer tube 1. The inflated balloon 4 has a shape capable of coming into close contact with the atrial muscles around ostium of the pulmonary vein ostium, such as a shape resembling an onion.

A guide wire 15 can be inserted into the inner tube 2 and a chemical solution can be injected into the inner tube 2.

The swirling current producing device 12 includes a vibration generator 16 for propagating a vibration through the fluid in a vibration propagating passage 14 between the inside surface 1a of the outer tube 1 and the outside surface 2a of the inner tube 2 to the fluid in the balloon 4, and a vibration propagating direction deflecting device 20 disposed near an end part of the vibration propagating passage corresponding to the inlet 18 of the balloon 4 to deflect the direction of propagation of a vibration propagated through the vibration propagating passage 14 upward or downward in the balloon 4.

The vibration generator 16 can generate a vibration of a waveform having a period of about 1 s. Referring to FIGS. 12 and 13, the period of the waveform of the vibration generated by the vibratory generator 16 includes a fluid ejection period 22 in which the fluid is ejected into the balloon 4 and a fluid suction period 23 in which the fluid in the balloon 4 is suctioned. As shown in FIG. 12, the fluid ejection period 22 is shorter than the fluid suction period 23, and a fluid ejection rate 24 at which the fluid is ejected in the fluid ejection period 22 is higher than a fluid suction rate 25 at which the fluid is suctioned in the fluid suction period 23. The vibrating generator 16 is controlled so that the product of the fluid ejection period 22 and the fluid ejection rate 24 is approximately equal to the product of the fluid suction period 23 and the fluid suction rate 25 to avoid the danger of the balloon 4 bursting due to the excessive accumulation of the fluid in the balloon 4. Any trouble will not occur even if the product of the fluid ejection period 22 and the fluid ejection rate 24 is different from the product of the fluid suction period 23 and the fluid suction rate 25 in some degree because the balloon 4 is made of the elastic material. FIG. 12(a) shows the waveform of the vibration generated by a vibration generator, FIG. 12(b) shows a mode of change of the volume of the balloon 4 during the ejection period 22, and FIG. 12(c) shows a mode of change of the volume of the balloon 4 during the suction period 23.

Energy for causing the unidirectional flow of the fluid in the balloon 4 can be imparted to the fluid by controlling the vibration generator 16 so that the fluid ejection period 22 is shorter than the fluid suction period 22, and the fluid ejection rate 24 in the fluid ejection period 22 is higher than the fluid suction rate 25 in the fluid suction period 23.

The vibration generator 16 may be controlled so that the fluid ejection period 22 is longer than the fluid suction period 22, and the fluid ejection rate 24 in the fluid ejection period 22 is lower than the fluid suction rate 25 in the fluid suction period 23 as shown in FIG. 13. When the vibratory generator 16 is controlled in a control mode for the conditions shown in FIG. 13, the direction of the swirling currents 10 in the balloon 4 is reverse to that of the swirling currents 10 in the balloon 4 when the vibratory generator 16 is controlled in a control mode for the conditions shown in FIG. 12.

The vibration propagating direction deflecting device 20 included in the swirling current producing device 12 deflects the direction of propagation of the vibration generated by the vibration generator 16 and propagated linearly through the vibration propagating passage 14 upward or downward in the balloon 4. When the direction of propagation of the vibration is thus deflected by the vibration propagating direction deflecting device 20, the swirling currents 10 swirling up and down is produced in the balloon 4 and the upper-lower temperature difference caused by convection in the balloon 4 is reduced to naught.

Figure 2:
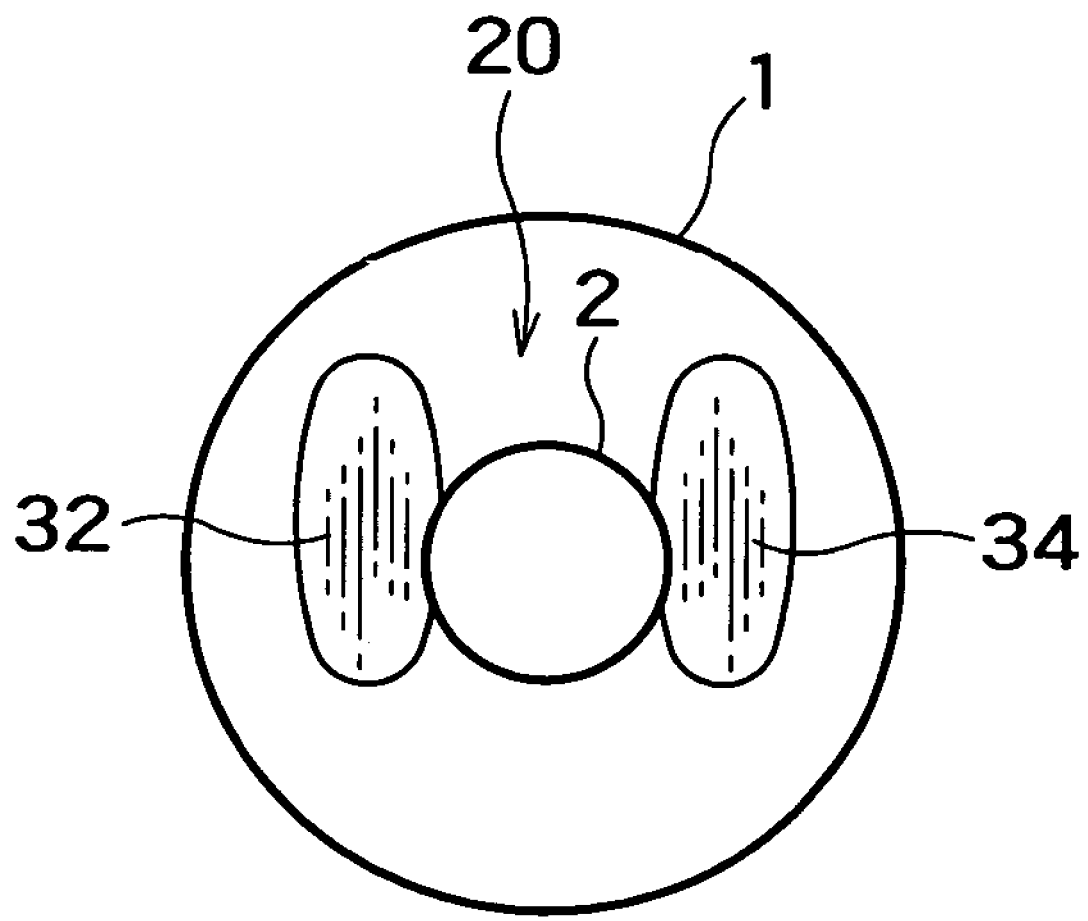
FIG. 2 is a sectional view, taken on the line A-A in FIG. 1, of a vibration propagating direction deflecting device included in the radio-frequency thermal balloon catheter shown in FIG. 1.

As shown in FIGS. 1 and 2, the vibration propagating direction deflecting device 20 included in the swirling current producing device 12 has a pair of elliptic blades 32 and 34. The blades 32 and 34 are disposed near the inlet 18 of the balloon 4 on the opposite sides, respectively, of the inner tube 2. The blades 32 and 34 are attached to the outside surface of the inner tube 2 and are inclined so as to deflect the propagating direction of the vibration propagating through the vibration propagating passage 14 downward in the balloon 4. The blades 32 and 34 may be inclined so as to deflect the propagating direction of the vibration propagating through the vibration propagating passage 14 upward in the balloon 4 to produce a swirling currents 10 swirling in a direction opposite the direction shown in FIG. 1.

The vibration generated by the vibration generator 16 is transmitted by the fluid filling up the vibration propagating passage 14 and is deflected so as to propagate downward in the balloon 4 by the blades 32 and 34. The fluid filling up the vibration propagating passage 14 does not flow into the balloon 4 and transmits the vibration. As shown in FIG. 12, since the waveform of the vibration is asymmetrical such that the fluid ejection period 22 is shorter than the fluid suction period 23, and the fluid ejection rate 24 at which the fluid is ejected in the fluid ejection period 22 is higher than the fluid suction rate 25 at which the fluid is suctioned in the fluid suction period 23, the unidirectional flow of the swirling currents 10 is produced in the balloon 4. Consequently, the fluid contained in the balloon 4 is stirred and the upper-lower temperature difference in the balloon 4 due to convection can be reduced to naught.

When the radio-frequency generator supplies radio-frequency power to the radio-frequency electrode 6 placed in the balloon 4 and the counter electrode 5 attached to the surface of the subject's body, the balloon 4 and the tissues in contact with the balloon 4 are heated by heat generated by the capacitive type heating between the radio-frequency electrode 6 and the counter electrode 5. The temperature sensor 8 measures the temperature of the fluid in the balloon 4, the output radio-frequency power of the radio-frequency generator 13 is controlled on the basis of the measured temperature measured by the temperature sensor 8 to maintain the fluid in the balloon 4 at a fixed optimum temperature. Consequently, atrial tissues 41 to be cauterized of the left atrium around the ostium of the pulmonary vein ostium are heated at an optimum temperature for cauterization.

Figure 9:
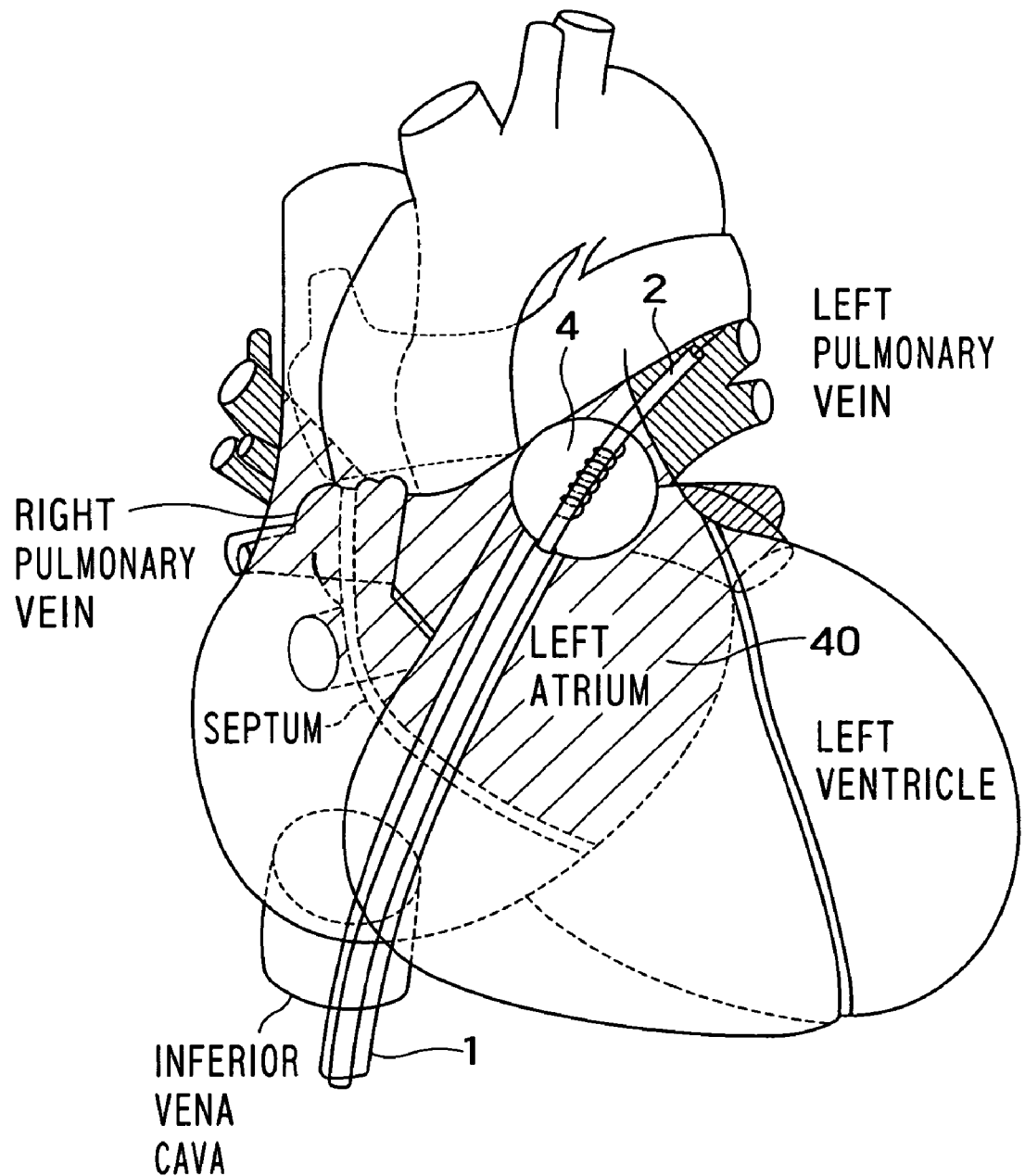
FIG. 9 is a view of assistance in explaining the cauterization of a lesion around the pulmonary vein ostium near the atrium by one of the radio-frequency thermal balloon catheters shown in FIGS. 1 to 6.

FIG. 9 is a view of assistance in explaining the cauterization of a lesion around ostium of the pulmonary vein ostium near the atrium by the radio-frequency thermal balloon catheter.

An operation for pumping physiological saline into and out of the balloon 4 with a pump 46 is repeated to deaerated the balloon 4. The balloon 4 is deflated and the inner tube 2 is slid forward relative to the outer tube 1 to a front end position to insert the radio-frequency balloon catheter into a blood vessel. Since the free end of the inner tube 2 is moved away from the free end of the outer tube 1, the diameter of the balloon 4 decreases to a minimum diameter. When the balloon 4 is inserted into the femoral vein in this state, a guide wire 15 and a guide sheath guide the balloon 4. The radio-frequency thermal balloon catheter is operated to bring the free end of the inner tube 2 near to the ostium of pulmonary vein ostium. Then, a contrast medium and physiological saline are injected into the balloon 4 while the inner tube 2 is being retracted to inflate the balloon 4 in a size greater than that ostium of the pulmonary vein ostium by a size between 5 and 10 mm. Then, the radio-frequency thermal balloon catheter is operated minutely to bring the balloon 4 into contact with target tissues of the left atrium around ostium of the pulmonary vein ostium. Then, the radio-frequency thermal balloon catheter is turned to bring the radiopaque mark 30 for indicating the predetermined attitude with respect to the vertical direction of the balloon 4 to a predetermined position. In this state, the blades 32 and 34 are disposed in an inclined attitude to deflect the direction of propagation of the vibration propagated through the vibration propagating passage 14 downward in the balloon 4. The radio-frequency thermal balloon catheter is turned to set the blades 32 and 34 in an inclined position as shown in FIG. 1, where a downward direction is the direction of the gravitational force.

The radio-frequency thermal balloon catheter disposed with the blades 32 and 34 inclined as shown in FIG. 1 is able to cauterize the atrial tissues 41 to be cauterized without any obstruction. Therefore, the radio-frequency thermal balloon catheter is effectively serviceable even if the radio-frequency thermal balloon catheter is turned to place the radiopaque mark 30 at the predetermined position.

A method of operating the radio-frequency thermal balloon catheter will be described. The vibration generator 16 is connected to the outer tube 1 by a connector. The vibration propagating passage 14 defined by the inside surface $1a$ of the outer tube 1 and the outside surface $2a$ of the inner tube 2, and the balloon 4 are filled up with a fluid. Then, the vibration generator 16 is turned on. A vibration 36 generated by the vibratory generator 16 is propagated through the vibration propagating passage 14. Then, the direction of propagation of the vibration 36 is deflected downward by the blades 32 and 34 disposed near the inlet 18 of the balloon 4. The vibration 36 propagated downward in the balloon 4 forces the fluid to flow vertically in the balloon 4. The vibration generator 16 drives the fluid so that the vibration 36 has a frequency and an amplitude as shown in FIG. 12. Consequently, swirling currents 10 swirling in a vertical plane is produced in the balloon 4 to stir the fluid contained in the balloon 4. Then, the radio-frequency generator 13 supplies a very high-frequency current of 13.56 MHz to the radio-frequency electrode 6 and the counter electrode 5. Consequently, the radio-frequency electrode 6 and the counter electrode 5 are connected by capacitive coupling and the balloon 4 and the atrial tissues 41 to be cauterized in contact with the balloon 4 are heated by capacitive type heating. There is an upper-lower temperature difference due to convection if the swirling currents 10 are not produced in the balloon 4. Since the fluid is stirred by the swirling currents 10 swirling in a vertical plane, there is not any upper-lower temperature difference in the fluid. Thus the tissues in contact with the balloon 4 are heated uniformly.

Suppose that the diameter of the ostium of the pulmonary vein ostium is 20 mm, the diameter of the inflated balloon 4 is 25 mm, and the length of the catheter tube 3 is 70 mm. Then, the swirling currents 10 of the fluid swirling in a vertical plane in the balloon 4 is produced when the frequency of the vibration generated by the vibratory generator 16 is 1 Hz and about 2.5 cm³ of the fluid is ejected into the balloon 4 every cycle of the vibration. Consequently, the upper-lower temperature difference due to convection is reduced to naught. When the temperature of the fluid in a central part of the balloon 4 is kept at about 75° C. by supplying power in the range of about 100 to 150 W by the radio-frequency generator 13, there will be an upper-lower temperature difference between 10° C. and 15° C. if the fluid is not stirred. Tests proved that the upper-lower temperature difference is 2° C. or below when the fluid is stirred by producing the swirling currents 10 in the balloon 4. Thus, the temperature difference between the fluid in the central part of the balloon 4 and the tissues in contact with the balloon 4 is about 10° C., and part of the balloon 4 in contact with the tissues can be adjusted to 65° C.±2° C. Consequently, the cauterization around the pulmonary vein ostium near the atrium can be achieved. Thus the atrial fibrillation originating from the pulmonary vein and tissues around the ostium the pulmonary vein ostium can be properly treated through the isolation of ostium of the pulmonary vein ostium and the cauterization of a part of the left atrium around ostium of the pulmonary vein ostium.

Figure 3:
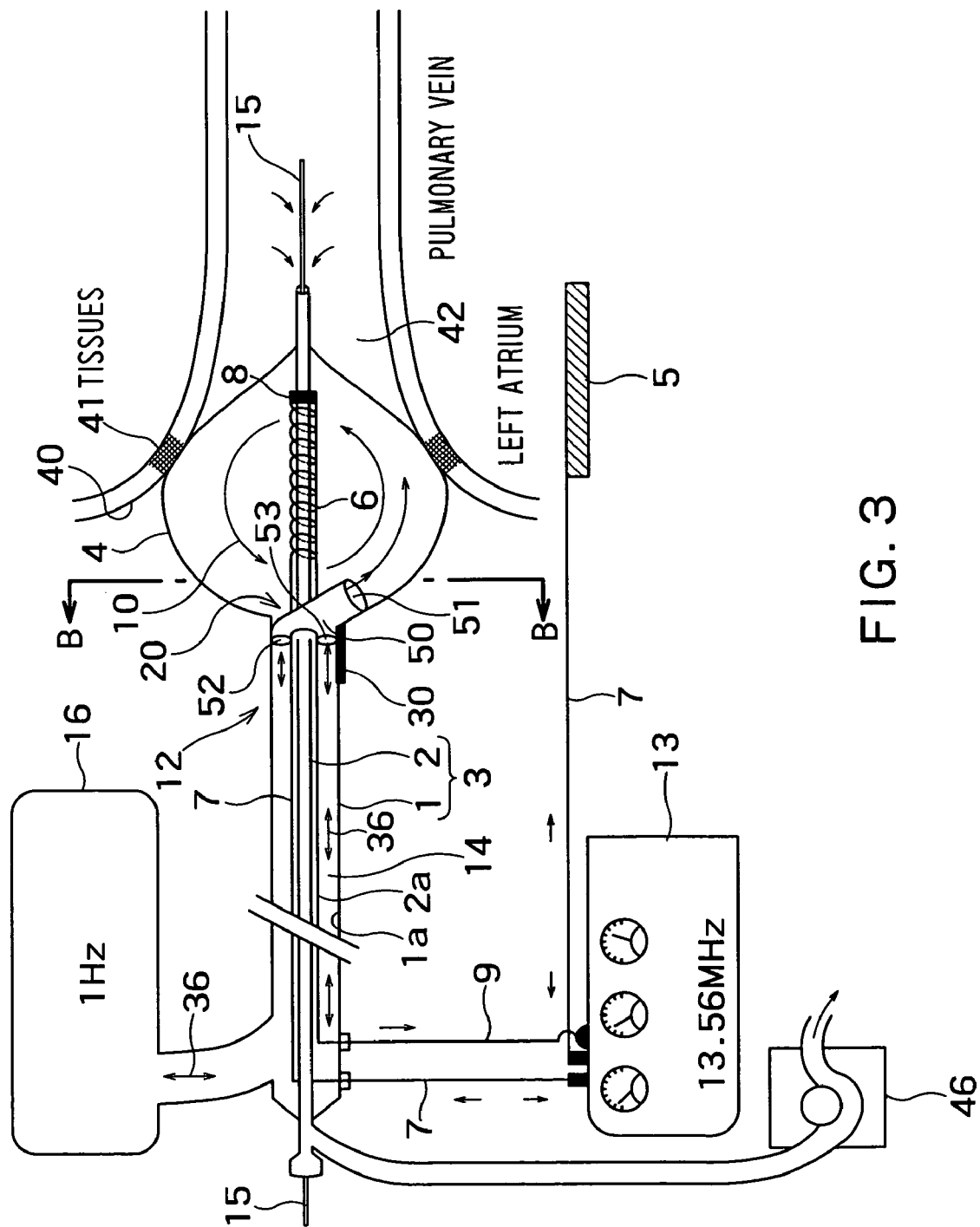
FIG. 3 is a schematic view of a radio-frequency thermal balloon catheter in a second embodiment according to the present invention.
Figure 4:
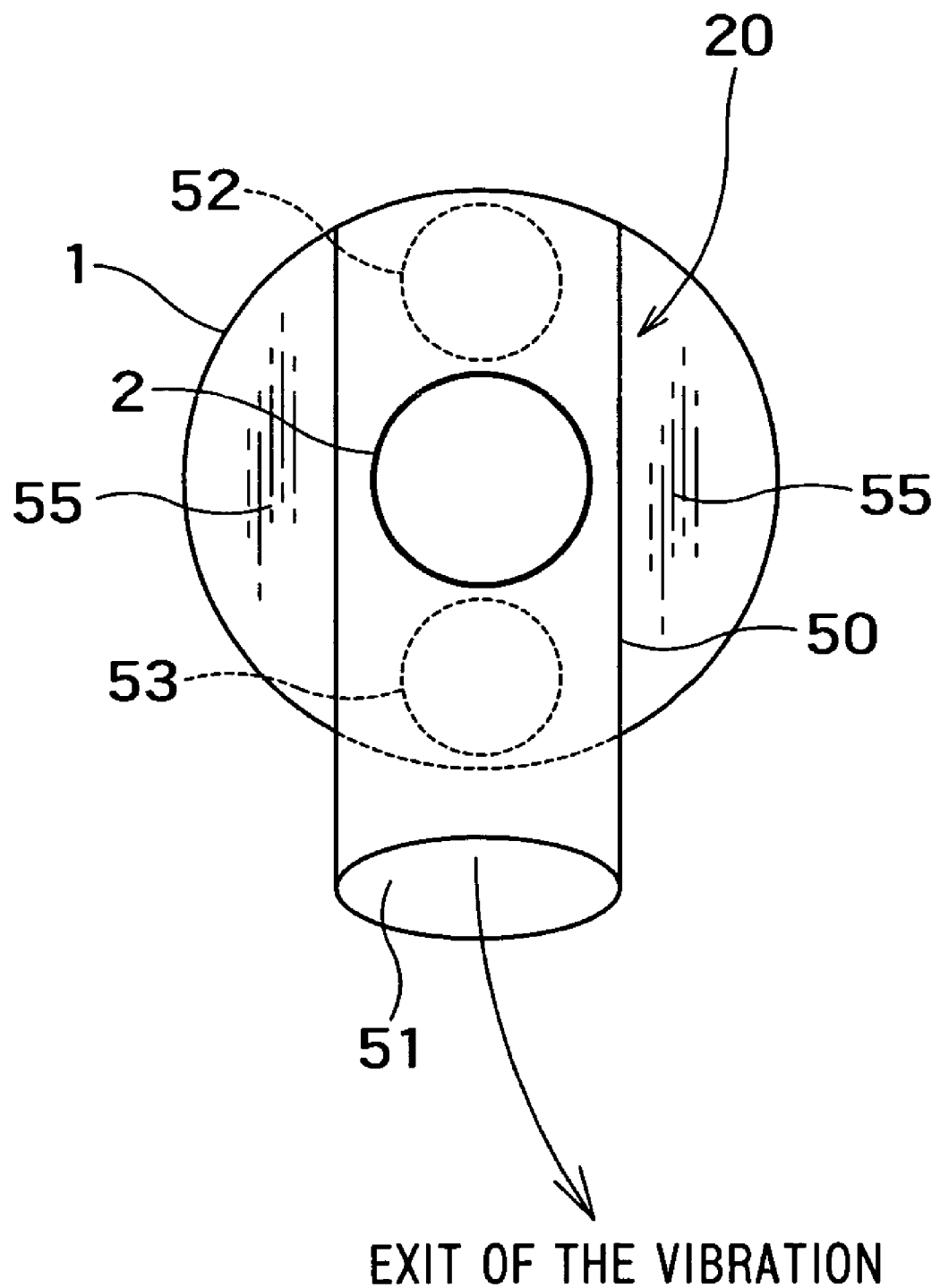
FIG. 4 is a sectional view, taken on the line B-B in FIG. 3, of a vibration propagating direction deflecting device included in the radio-frequency thermal balloon catheter shown in FIG. 3.

A radio-frequency thermal balloon catheter in a second embodiment according to the present invention will be described with reference to FIGS. 3 and 4. Description of matters the same as those of the first embodiment, such as an operation for controlling a ejection rate 24 at which a vibration generator 16 ejectes a fluid and a suction rate at which the vibration generator 16 suctions the fluid, will be omitted.

In the radio-frequency thermal balloon catheter in the second embodiment, a vibration propagating direction deflecting device 20 includes a pipe 50 disposed near the inlet 18 of a balloon 4. The pipe has an open end 51 and a closed end. A first hole 52 and a second hole 53 are formed in the same side of the pipe 50. An inner tube 2 penetrates the pipe 50 closely. The first hole 52 and the second hole 53 are on the opposite sides, respectively, of the inner tube 2. As shown in FIG. 4, the pipe 50 is held on a holding plate 55 fitted in an outer tube 1 and joined to the inside surface of the outer tube 1. Since the interior of the outer tube 1 is partitioned by the holding plate 55, a vibration propagating passage 14 communicates with the interior of the balloon 4 by means of the open end 51, the first hole 52 and the second hole 53 of the pipe 50. The pipe 50 is inclined as shown in FIG. 3 to deflect the direction of propagation of a vibration propagated through the vibration propagating passage 14 downward in the balloon 4.

The radio-frequency thermal balloon catheter is turned so as to place an radiopaque mark 30 at a predetermined position so that the pipe 50 is inclined to deflect the direction of propagation of the vibration downward in the balloon 4. When a downward direction in FIG. 3 is parallel to the direction of the gravitational force, the radio-frequency thermal balloon catheter may be turned to place the pipe 50 at a position shown in FIG. 3. There is an upper-lower temperature difference due to convection if the swirling currents 10 swirling in a vertical plane are not produced in the balloon 4. Since the fluid is stirred by the swirling currents 10 swirling in a vertical plane, there is not any upper-lower temperature difference in the fluid. Thus tissues 41 in contact with the balloon 4 can be uniformly heated.

Figure 5:
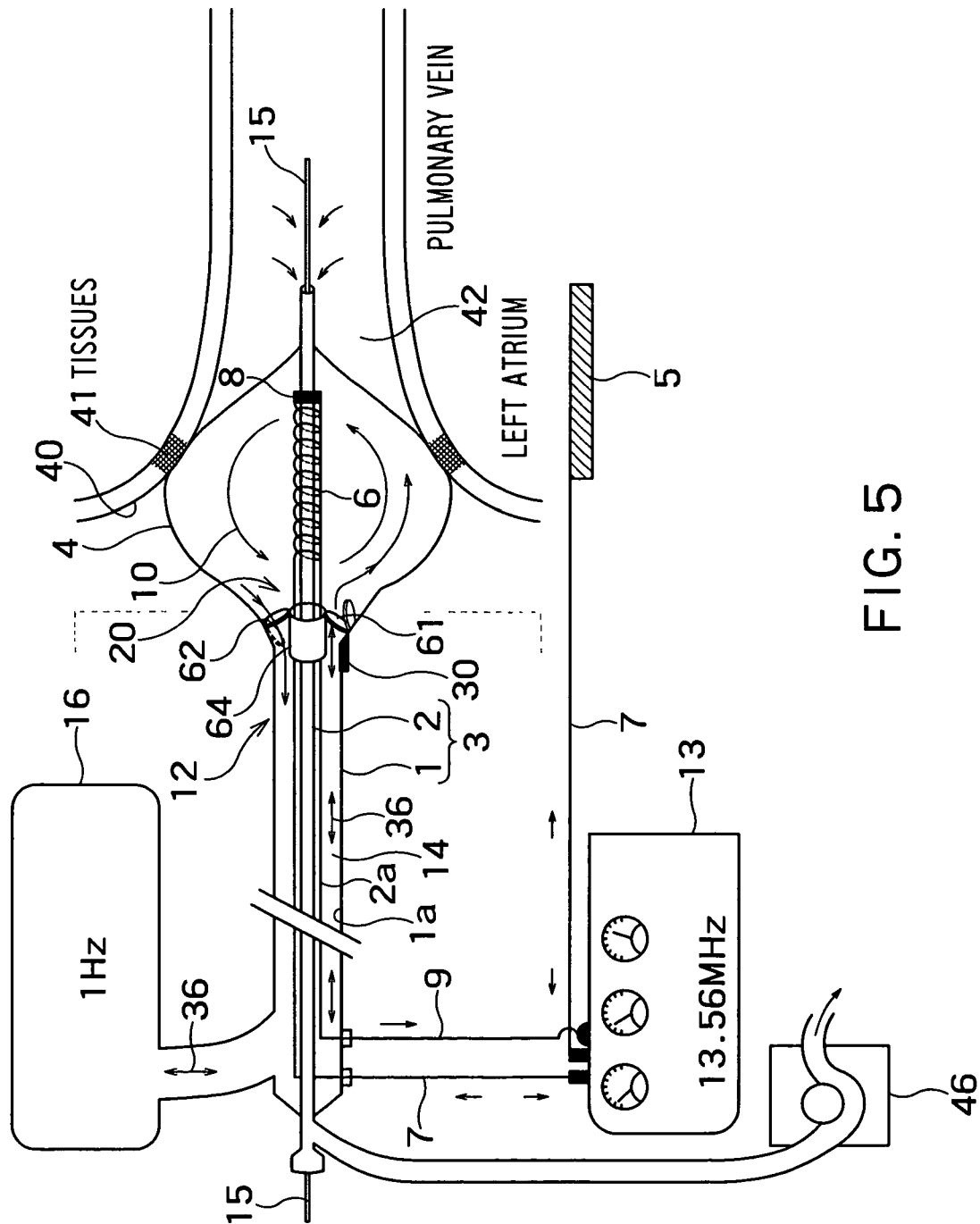
FIG. 5 is a schematic view of a radio-frequency thermal balloon catheter in a third embodiment according to the present invention.
Figure 6:
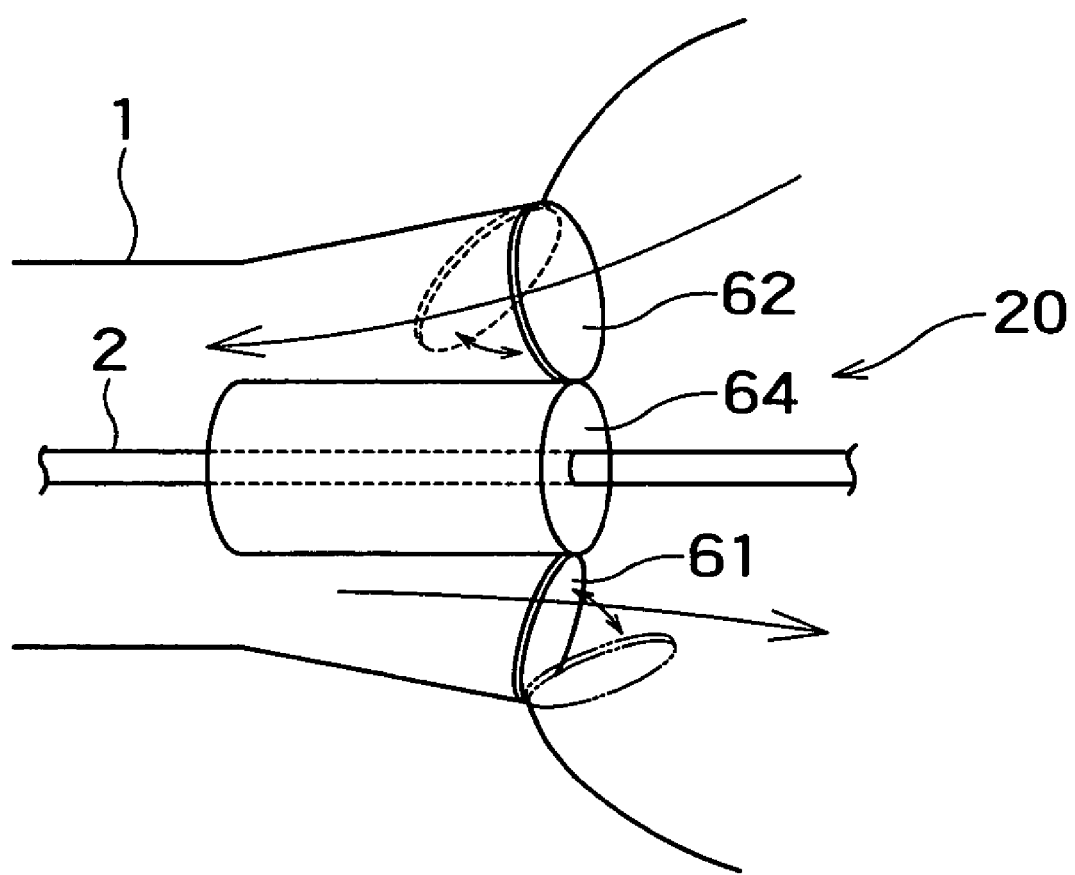
FIG. 6 is a sectional view, taken on the line C-C in FIG. 5, of a vibration propagating direction deflecting device included in the radio-frequency thermal balloon catheter shown in FIG. 5.

A radio-frequency thermal balloon catheter in a third embodiment according to the present invention will be described with reference to FIGS. 5 and 6. Description of matters the same as those of the first embodiment, such as an operation for controlling a ejection rate 24 at which a vibration generator 16 ejectes a fluid and a suction rate at which the vibration generator 16 suctions the fluid, will be omitted.

In the radio-frequency thermal balloon catheter in the second embodiment, a vibration propagating direction deflecting device 20 includes unidirectional valves 61 and 62 disposed near the inlet 18 of a balloon 4. A holding member 64 is attached to a part of an inner tube 2 near the inlet 18 of the balloon 4, and the unidirectional valves 61 and 62 are held in a space between the holding member 64 and the inside surface of an outer tube 1. The unidirectional valves 61 and 62 are disposed on the lower side and the upper side, respectively, of the inner tube 2. The unidirectional valve 61 opens when the fluid is ejected into the balloon 4 and the unidirectional valve 62 opens when the fluid is suctioned from the balloon 4.

The radio-frequency thermal balloon catheter is turned so as to place an radiopaque mark 30 at a predetermined position. When the radiopaque 30 is placed at the predetermined position, the unidirectional valves 61 and 62 are arranged vertically. The direction of propagation of a vibration propagated through a vibration propagating passage 14 is deflected by the unidirectional valve 61 downward to produce swirling currents 10 in the balloon 4. The vibration is propagated from the balloon 4 through the unidirectional valve 62 into the vibration propagating passage 14. There is an upper-lower temperature difference due to convection if the swirling currents 10 swirling in a vertical plane are not produced in the balloon 4. Since the fluid is stirred by the swirling currents 10 swirling in a vertical plane, there is not any upper-lower temperature difference in the fluid. Thus tissues 41 in contact with the balloon 4 can be uniformly heated.

A radio-frequency thermal balloon catheter in a fourth embodiment according to the present invention will be described with reference to FIG. 7. Description of matters the same as those of the first embodiment, such as an operation for controlling a ejection rate 24 at which a vibration generator 16 ejectes a fluid and a suction rate at which the vibration generator 16 suctions the fluid, will be omitted.

Figure 7:
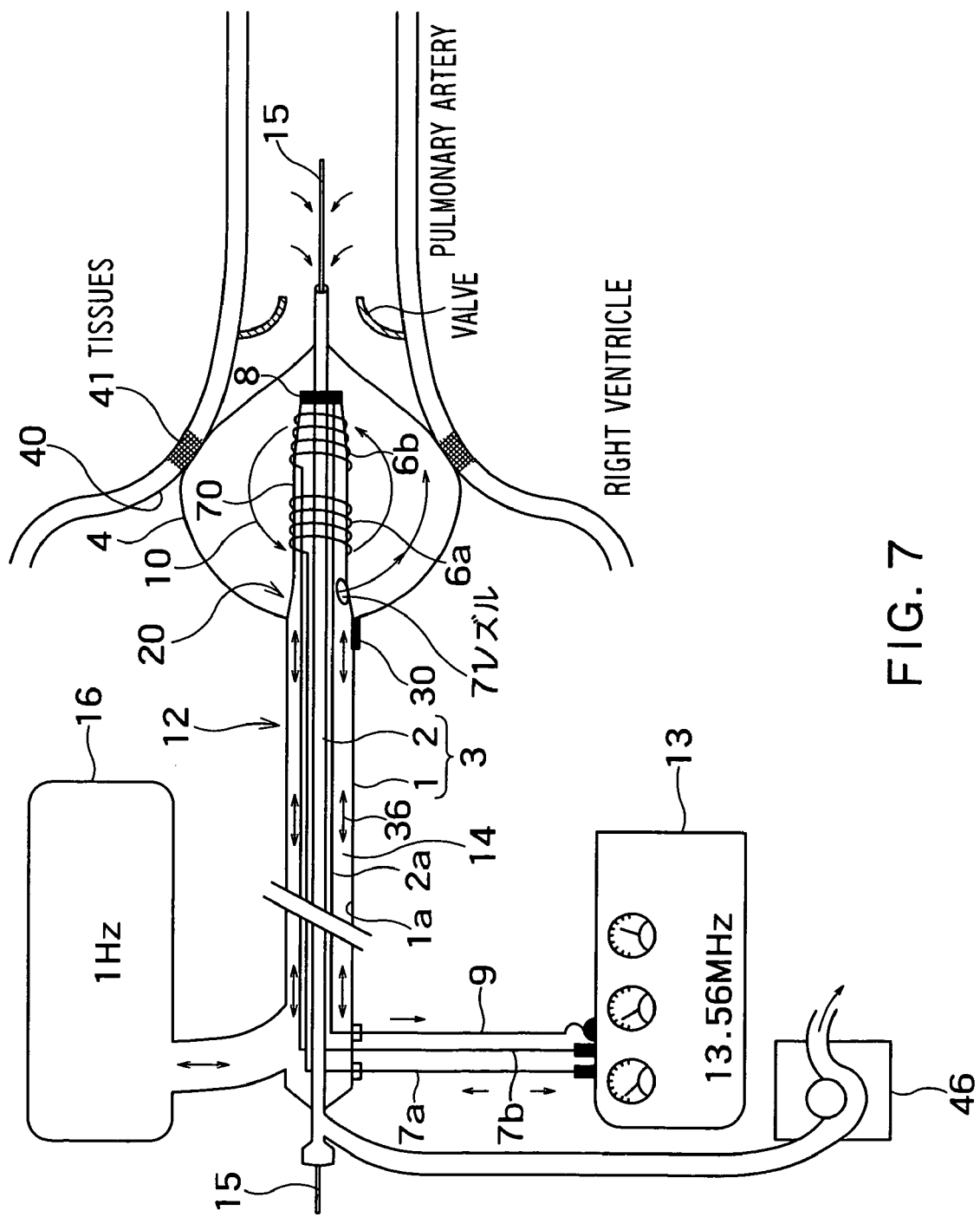
FIG. 7 is a schematic view of a radio-frequency thermal balloon catheter in a fourth embodiment according to the present invention in use for treating an origin for ventricular tachycardia and ventricular fibrillation originating from the outflow tract of the right ventricle.

In the radio-frequency thermal balloon catheter shown in FIG. 7, a large balloon 4 is connected to respective end parts of an outer tube 1 and an inner tube 2 slidable relative to the outer tube 1. The diameter of the inflated balloon 4 is between 25 and 35 mm.

A vibration propagating direction deflecting device 20 includes an extension tube 70 having a closed tip and provided with an opening 71 in its lower side. A pair of radio-frequency electrodes 6a ad 6b are wound round the extension tube 70. This radio-frequency thermal balloon catheter in the fourth embodiment does not use any counter electrode to be attached to the surface of the subject's body. The radio-frequency electrodes 6a and 6b are connected to a radio-frequency generator 13 respectively by lead wires 7a and 7b.

The radio-frequency thermal balloon catheter is turned so as to place an radiopaque mark 30 at a predetermined position so that the opening 71 opens downward to deflect the direction of propagation of a vibration propagated through a vibration propagating passage 14 downward in the balloon 4. The vibration propagated downward in the balloon 4 produces whirling currents 10 in the balloon 4. The vibration is propagated from the balloon 4 through the opening 71 into the vibration propagating passage 14. There is an upper-lower temperature difference due to convection if the swirling currents 10 swirling in a vertical plane are not produced in the balloon 4. Since the fluid is stirred by the swirling currents 10 swirling in a vertical plane, there is not any upper-lower temperature difference in the fluid. Thus tissues 41 in contact with the balloon 4 can be uniformly heated.

Figure 10:
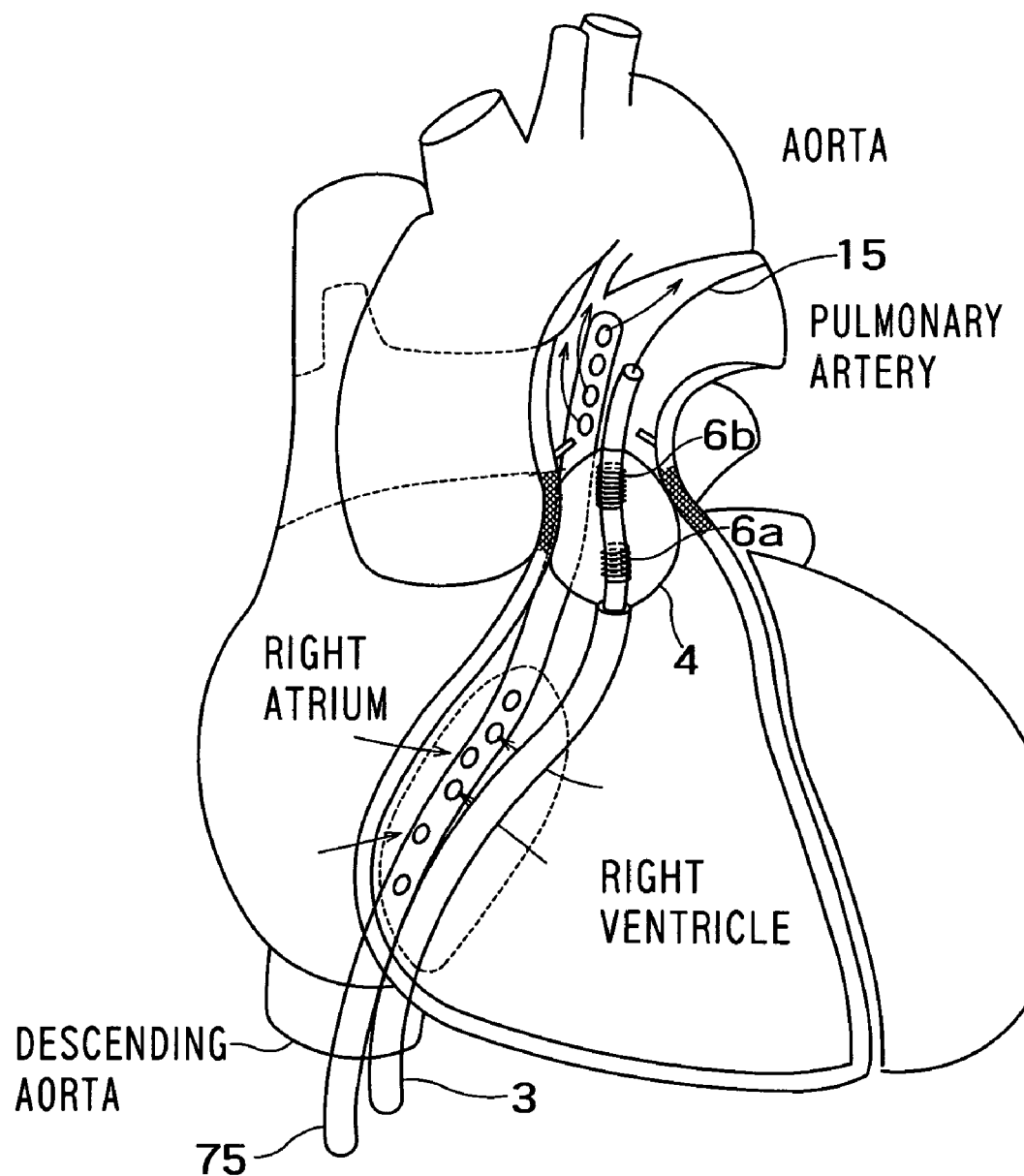
FIG. 10 is a view of assistance in explaining the treatment of a lesion for ventricular tachycardia and ventricular fibrillation at the outflow tract of the right ventricle the radio-frequency thermal balloon catheters shown in FIG. 7.

Application of the radio-frequency thermal balloon catheter shown in FIG. 7 to the treatment for tachycardia and ventricular fibrillation originating from the outflow tract of the right ventricle will be described with reference to FIG. 10.

The inner tube 2 is pushed out so as to increase the distance between the end part of the outer tube 1 to which one end of the balloon 4 is connected and the end part of the inner tube 1 to which the other end of the balloon 4 is connected to make the balloon 4 shrink. The guide wire 15 is percutaneously inserted through the femoral vein into the pulmonary artery. The radio-frequency thermal balloon catheter is inserted along the guide wire 15 into the exit of the right ventricle. Then, a leading end part of a pulmonary blood perfusion catheter 75 is inserted through the opposite femoral vein into the pulmonary vein. The radio-frequency thermal balloon catheter is turned to place the radiopaque mark 30 is on the lower side. Then, the balloon 4 is inflated by injecting a contrast medium and physiological saline into the balloon 4 while the inner tube 2 is being retracted so as to decrease the distance between the opposite ends of the balloon 4. Consequently, the wall of the balloon 4 is pressed against the outflow tract of the right ventricle. Then, the vibration generator 13 is actuated to generate a vibration and the frequency and amplitude of the vibration are regulated. The vibration is propagated through the vibration propagating passage 14. The vibration is propagated through the opening 71 formed in the lower side of the extension tube 70 downward in the balloon 4 to produce whirling currents 10 in the balloon 4. The temperature of the fluid in the balloon 4 is monitored and the output radio-frequency power is regulated to keep the fluid contained in the balloon 4 at about 75° C. The pump 46 pumps cooling water into the inner tube 2 to prevent the radio-frequency electrodes 6a and 6b from being excessively heated. The effective temperature of the balloon 4 is about 65° C. Radio-frequency power is supplied to the radio-frequency electrodes 6a and 6b for a time between 3 and 5 min to cauterize a part of the outflow tract of the right ventricle originating arrhythmia uniformly and transmurally for the radical treatment of the arrhythmia originated from the outflow tract of the right ventricle for arrhythmia.

A radio-frequency thermal balloon catheter in a fifth embodiment according to the present invention will be described with reference to FIG. 8. Description of matters the same as those of the first embodiment, such as an operation for controlling a ejection rate 24 at which a vibration generator 16 ejectes a fluid and a suction rate at which the vibration generator 16 suctions the fluid, will be omitted.

Figure 8:
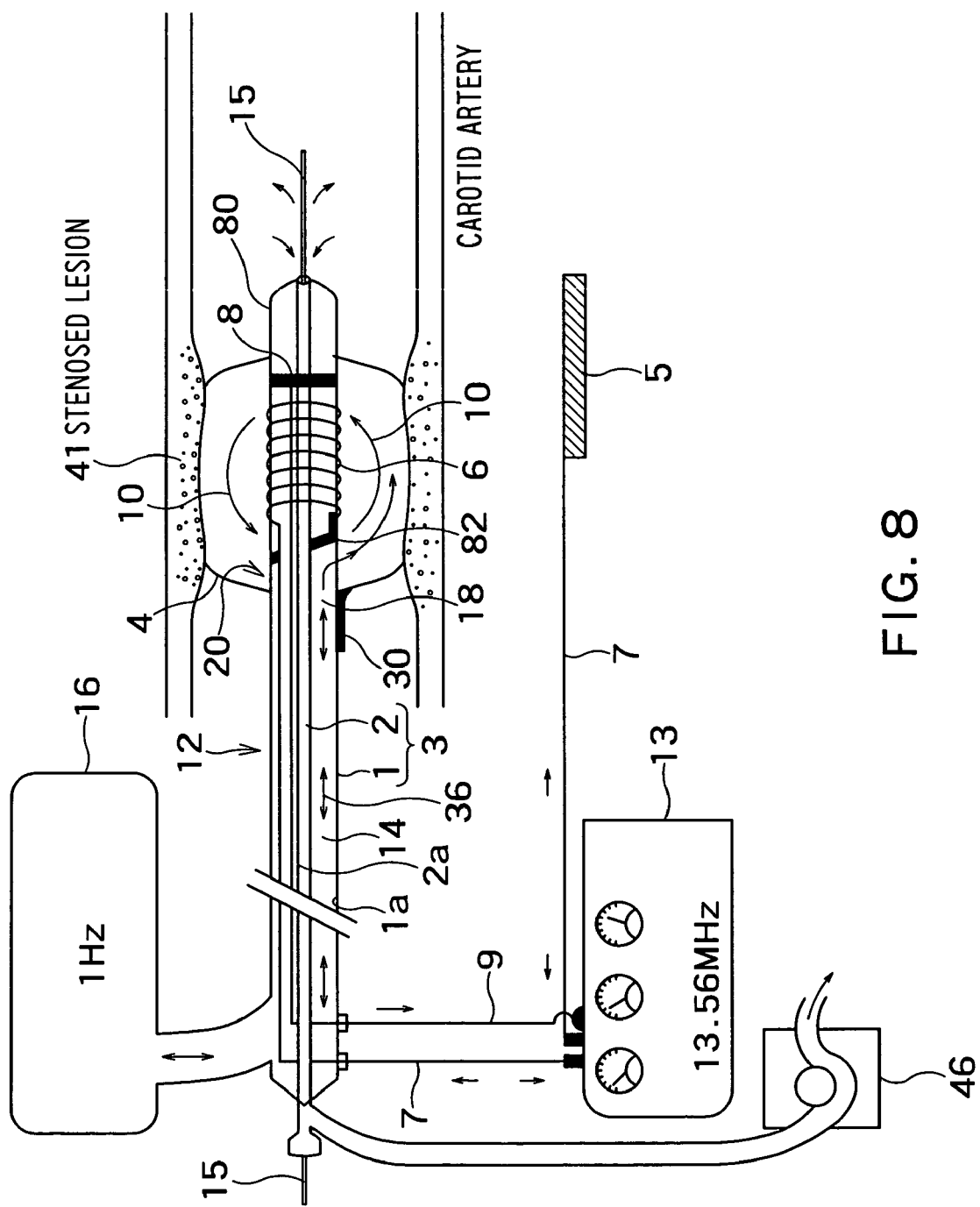
FIG. 8 is a schematic view of a radio-frequency thermal balloon catheter in a fifth embodiment according to the present invention in use for treating tissues affected by arteriosclerosis.

In the radio-frequency thermal balloon catheter shown in FIG. 8, a vibration propagating direction deflecting device 20 includes an extension tube 80 connected to the free end of an outer tube 1 and having a closed tip, and a branch tube 82 connected to the extension tube 80. An end part of the extension tube 80 projects forward from the front side of a balloon 4. A front end part of the balloon 4 is connected to the end part of the extension tube 80. The tip of an inner tube 2 is joined to the front end of the extension tube 80. Since the inner tube 2 is not slidable relative to the outer tube 1, the balloon 4 cannot be extended and contracted by sliding the inner tube 2 relative to the outer tube 1. However, the balloon 4 is able to cauterize a lesion, such as atherosclerosis, without complications.

The radio-frequency thermal balloon catheter is turned so as to place an radiopaque mark 30 at a predetermined position so that the branch tube 82 is placed at a lower position. Consequently, the direction of propagation of a vibration propagated through the vibration propagating passage 14 is deflected downward by the branch tube 82. The vibration propagated downward in the balloon 4 produces whirling currents 10 in the balloon 4. The vibration is propagated from the balloon 4 through the branch tube 82 into the vibration propagating passage 14. There is an upper-lower temperature difference due to convection if the swirling currents 10 swirling in a vertical plane are not produced in the balloon 4. Since the fluid is stirred by the swirling currents 10 swirling in a vertical plane, there is not any upper-lower temperature difference in the fluid. Thus atherosclerotic tissues 41 of a blood vessel in contact with the balloon 4 can be uniformly heated.

Figure 11:
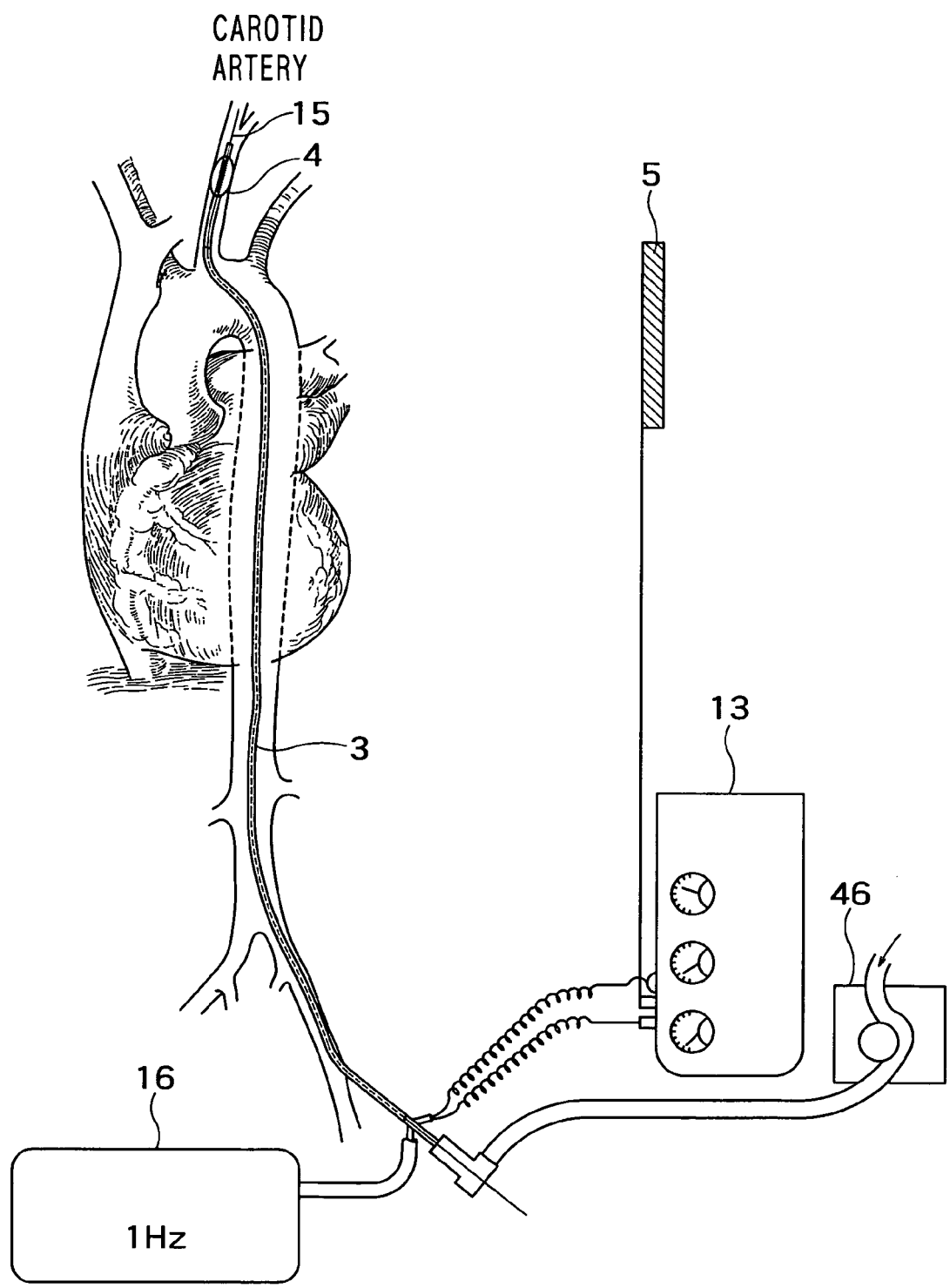
FIG. 11 is a view of assistance in explaining the treatment of tissues affected by arteriosclerosis by the radio-frequency thermal balloon catheter shown in FIG. 8.

Application of the radio-frequency thermal balloon catheter shown in FIG. 8 to the treatment of a lesion of atherosclerosis with reference to FIG. 11.

The balloon 4 of the radio-frequency thermal balloon catheter shown in FIG. 8 intended for the treatment of a lesion of the carotid artery has a diameter between 5 and 10 mm in an inflated state.

The balloon 4 of the radio-frequency thermal balloon catheter is deflated and the radio-frequency thermal balloon catheter is inserted through the femoral artery into the carotid artery to bring the balloon 4 into contact with a diseased part 41 of the carotid artery. Then, the balloon 4 is inflated by injecting a mixture of a contrast medium and physiological saline into the balloon 4 through an inlet formed in the outer tube 1 and a supply passage to press the balloon 4 against a stenosed part of the carotid artery. Then, radio-frequency power is supplied to a radio-frequency electrode and a counter electrode 5 while the temperature in the balloon 4 is monitored. At the same time, a vibration generator 16 is actuated to propagate a vibration through a vibration propagating passage 14. The direction of propagation of the vibration is deflected downward by the branch tube 82 to produce whirling currents 10 whirling in a vertical plane in the balloon 4. The swirling currents 10 stir the fluid contained in the balloon 4 to reduce an upper-lower temperature difference that may be otherwise caused by convention to naught. Thus the fluid contained in the balloon 4 can be uniformly heated. A pump 46 pumps cooling water into the inner tube 2 to prevent distal parts of the carotid artery from being cauterized. The working part of the balloon 4 is kept at about 43.5° C. and the diseased part is heated for about 20 min. Consequently, the Apotosis of inflammatory cells, such as macrophages, in the lesion in contact with the balloon 4 occurs and thereby tissues affected by arteriosclerosis can be stabilized. If the diseased part 41 of the carotid artery is greatly stenosed, the stenosed diseased part 41 can be expanded by increasing the pressure in the balloon 4. If the diseased part 41 is heavily sclerosed and cannot be easily expanded, the fluid contained in the balloon 4 is heated at temperatures in the range of 50° C. to 60° C. and the pressure in the balloon 4 is increased to expand the stenosed lesion 41. After the completion of the treatment, the balloon 4 is deflated and the radio-frequency thermal balloon catheter is extracted from the carotid artery and the femoral artery.

The invention claimed is:

1. A radio-frequency thermal balloon catheter comprising:
a catheter tube including an outer tube having an end part and an inside surface and an inner tube having an end part and an outside surface, the inside surface of the outer tube and the outside surface of the inner tube defining a vibration propagation passage having an end;
a balloon connected to the end part of the outer tube and the end part of the inner tube, and capable of coming into contact with a target diseased part when inflated, the balloon including an inlet, a wall, and an interior having an upper part and a lower part, the upper part being positioned upwardly and the lower part being positioned downwardly with respect to the direction of the gravitational force;
a high-frequency electrode placed in the wall of the balloon or inside the balloon to transmit high-frequency power;
a lead wire electrically connected to the high-frequency electrode;
a temperature sensor capable of measuring temperature inside the balloon; and
a swirling current producing unit configured to make a fluid contained in the balloon swirl in a vertical plane in the balloon so as to reduce an upper-lower temperature difference between the upper part and the lower part of the interior of the balloon due to convection of the fluid to naught, the vertical plane being positioned to be parallel to the direction of the gravitational force;
wherein the swirling current producing unit includes a vibratory driving unit configured to propagate a vibration through the fluid filling up the vibration propagating passage to the fluid filling up the balloon, and a vibration propagating direction deflecting unit disposed near the inlet of the balloon at the end of the vibration propagating passage to deflect the direction of propagation of the vibration upward or downward with respect to the direction of the gravitational force in the balloon,
wherein the catheter tube is marked with a mark indicating a position of the balloon with respect to the direction of the gravitational force, and a position and an attitude of the vibration propagating direction deflecting unit are adjustable with respect to the direction of the gravitational force by referring to the mark, and
wherein a period of the vibration generated by the vibratory driving unit includes a fluid ejection period in which the fluid is ejected into the balloon and a fluid suction period in which the fluid in the balloon is suctioned, and
the fluid ejection period is shorter than the fluid suction period and a fluid ejection rate at which the fluid is ejected in the fluid ejection period is higher than a fluid suction rate at which the fluid is suctioned in the fluid suction period, or the fluid ejection period is longer than the fluid suction period and a fluid ejection rate at which the fluid is ejected in the fluid ejection period is lower than a fluid suction rate at which the fluid is suctioned in the fluid suction period.

2. The radio-frequency thermal balloon catheter according to claim 1, wherein the product of the fluid ejection period and the fluid ejection rate in the vibration generated by the vibratory driving unit is equal to the product of the fluid suction period and the fluid suction rate.

3. The radio-frequency thermal balloon catheter according to claim 1, wherein the vibration propagating direction deflecting unit includes a pair of blades disposed on the opposite sides of the inner tube near the inlet, each of the pair of blades is inclined so as to deflect the direction of propagation of the vibration propagated through the vibration propagating passage into the balloon upward or downward with respect to the direction of the gravitational force in the balloon.

4. The radio-frequency thermal balloon catheter according to claim 1, wherein the vibration propagating direction deflecting unit includes an extension tube having an open end and a bottomed end and provided with first and second holes in its wall, the inner tube extends through the wall of the extension tube disposed with the first and the second hole vertically arranged, and the extension tube is inclined so as to deflect the direction of propagation of the vibrations propagated through the vibration propagating passage into the balloon upward or downward with respect to the direction of the gravitational force in the balloon.

5. The radio-frequency thermal balloon catheter according to claim 1, wherein the inner tube includes upper and lower sides, and the vibration propagating direction deflecting unit includes a pair of unidirectional valves disposed on the upper and the lower sides of the inner tube near the inlet, one of the unidirectional valve opens to permit ejection of the fluid into the balloon and the other unidirectional valve opens to permit suction of the fluid out of the balloon.

6. The radio-frequency thermal balloon catheter according to claim 1, wherein the vibration propagating direction deflecting unit includes an extension tube extending from the outer tube and having a closed end, and either an upper or a lower side part of the extension tube is provided with an opening.

7. The radio-frequency thermal balloon catheter according to claim 1, wherein the vibration propagating direction deflecting unit includes an extension tube extending from the outer tube and having a closed end, and a branch tube extending from either an upper or a lower side part of the extension tube.

8. The radio-frequency thermal balloon catheter according to claim 1, wherein the mark is radiopaque.

9. The radio-frequency thermal balloon catheter according to claim 1, wherein the electrode is wound spirally around the inner tube.

10. The radio-frequency thermal balloon catheter according to claim 1, wherein the balloon is made of an anti-thrombotic, heat-resistant, and elastic resin.

11. The radio-frequency thermal balloon catheter according to claim 1, wherein the swirling current producing unit is configured to deflect the propagating vibration in one of an upward direction and a downward direction so as to generate a unidirectional flow of the fluid contained in the balloon.

* * * * *